(12) United States Patent
Desjardin et al.

(10) Patent No.: US 11,471,189 B2
(45) Date of Patent: Oct. 18, 2022

(54) SURGICAL ACCESS DEVICE WITH FIXATION MECHANISM AND ILLUMINATION MECHANISM

(71) Applicant: Covidien LP, Mansfield, MA (US)

(72) Inventors: Kevin M. Desjardin, Prospect, CT (US); Garrett P. Ebersole, Hamden, CT (US); Astley C. Lobo, West Haven, CT (US)

( * ) Notice: Subject to any disclaimer, the term of this patent is extended or adjusted under 35 U.S.C. 154(b) by 79 days.

(21) Appl. No.: 17/083,916

(22) Filed: Oct. 29, 2020

(65) Prior Publication Data

US 2022/0133351 A1    May 5, 2022

(51) Int. Cl.
*A61B 17/34* (2006.01)
*A61B 90/30* (2016.01)

(52) U.S. Cl.
CPC .......... *A61B 17/3423* (2013.01); *A61B 90/30* (2016.02); *A61B 2017/3425* (2013.01); *A61B 2017/3492* (2013.01); *A61B 2090/309* (2016.02)

(58) Field of Classification Search
CPC ................ A61B 17/3423; A61B 90/30; A61B 2017/3492; A61B 2090/309
USPC .................. 600/184–249; 606/108, 190–194
See application file for complete search history.

(56) References Cited

U.S. PATENT DOCUMENTS

| 397,060 | A | 1/1889 | Knapp |
|---|---|---|---|
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari et al. |
| 3,713,447 | A | 1/1973 | Adair |
| 3,774,596 | A | 11/1973 | Cook |

(Continued)

FOREIGN PATENT DOCUMENTS

| EP | 0480653 A1 | 4/1992 |
|---|---|---|
| EP | 0610099 A2 | 8/1994 |

(Continued)

OTHER PUBLICATIONS

Extended European Search Report dated Mar. 31, 2022 issued in corresponding EP Appln. No. 21209207.6.

*Primary Examiner* — Eduardo C Robert
*Assistant Examiner* — Tara Rose E Carter
(74) *Attorney, Agent, or Firm* — Carter, DeLuca & Farrell LLP

(57) ABSTRACT

A surgical access device includes a cannula body, a fixation mechanism, and an illumination mechanism. The fixation mechanism includes a collar, a sleeve, an expandable member, and a distal ring. The illumination mechanism includes at least one light disposed on the expandable member, and a switch. Distal translation of the collar relative to an elongated portion of the cannula body causes the expandable member to move from a first position defining a first gap between a mid-portion of the expandable member and the elongated portion of the cannula body, to a second position defining a second gap between the mid-portion of the expandable member and the elongated portion of the cannula body, the second gap being greater than the first gap.

17 Claims, 8 Drawing Sheets

(56) References Cited

U.S. PATENT DOCUMENTS

| | | |
|---|---|---|
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A * | 3/1994 | Foster ............... A61B 17/34 604/174 |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 8,454,645 B2 | 6/2013 | Criscuolo et al. |
| 10,751,086 B2 | 8/2020 | Shipp et al. |
| 2006/0079925 A1 | 4/2006 | Kerr |
| 2008/0287740 A1 | 11/2008 | Weitzner et al. |
| 2011/0144440 A1* | 6/2011 | Cropper ............ A61B 17/3421 600/203 |
| 2011/0144447 A1 | 6/2011 | Schleitweiler et al. |
| 2013/0053782 A1 | 2/2013 | Shelton, IV |

(56) References Cited

U.S. PATENT DOCUMENTS

2015/0297260 A1   10/2015  Kreuz et al.
2015/0366583 A1*  12/2015  Druma ............... A61B 17/0293
                                                                     600/204
2016/0038018 A1    2/2016  Wilson et al.

FOREIGN PATENT DOCUMENTS

| EP | 0880939 | A1 | 12/1998 |
| --- | --- | --- | --- |
| WO | 9206638 | A1 | 4/1992 |
| WO | 9218056 | A1 | 10/1992 |
| WO | 9221293 | A1 | 12/1992 |
| WO | 9221295 | A1 | 12/1992 |
| WO | 9309722 | A1 | 5/1993 |
| WO | 9721461 | A1 | 6/1997 |
| WO | 9912602 | A1 | 3/1999 |
| WO | 0126724 | A2 | 4/2001 |
| WO | 02096307 | A2 | 12/2002 |
| WO | 2004032756 | A2 | 4/2004 |

* cited by examiner

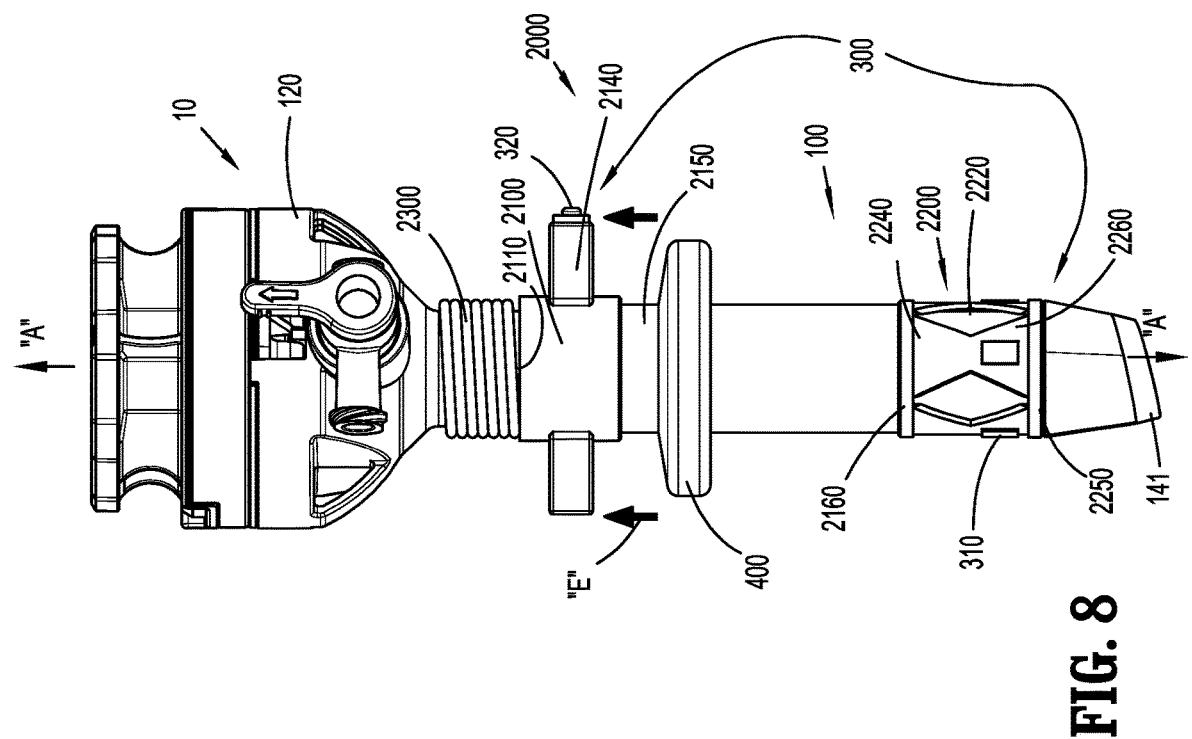
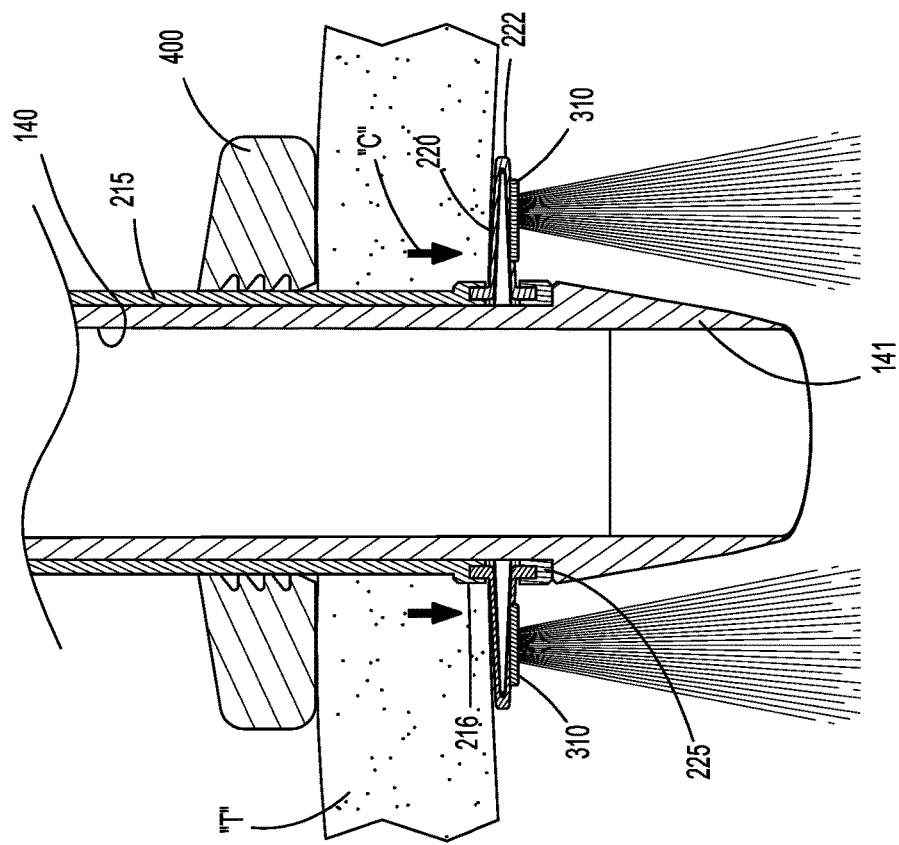
FIG. 7
FIG. 8

SURGICAL ACCESS DEVICE WITH FIXATION MECHANISM AND ILLUMINATION MECHANISM

BACKGROUND

Technical Field

The present disclosure relates to a surgical access device. More particularly, the present disclosure relates to a surgical access device having a fixation mechanism to help maintain its position relative to a patient during a surgical procedure and an illumination mechanism to help illuminate a surgical site.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an expandable anchor or fixation mechanism disposed near a distal end of the surgical access device is occasionally used. Expanding such an anchor while the surgical access device is within the body helps prevent the surgical access device from undesired movement with respect to the body.

Additionally, during such surgical procedures, it may be challenging for a user to see the surgical site even when an endoscope or laparoscope with a camera and light source are being utilized.

Accordingly, it may be helpful to provide a fixation mechanism to help maintain the longitudinal position of the surgical access device with respect to the patient, and it may be helpful to include a light source on a portion of the surgical access device to help illuminate the surgical site.

SUMMARY

The present disclosure relates to a surgical access device including a cannula body, a fixation mechanism, and an illumination mechanism. The cannula body includes a housing and an elongated portion extending distally from the housing. The elongated portion defines a longitudinal axis, and defines a channel extending therethrough. The fixation mechanism is disposed in mechanical cooperation with the elongated portion of the cannula body, and includes a collar, a sleeve, an expandable member, and a distal ring. The collar at least partially surrounds a portion of the elongated portion of the cannula body, and is longitudinally translatable relative to the elongated portion of the cannula body. The sleeve extends distally from the collar. The expandable member extends distally from the sleeve and radially surrounds a portion of the elongated portion of the cannula body. The distal ring is engaged with a distal portion of the expandable member and is longitudinally fixed relative to the elongated portion of the cannula body. The illumination mechanism is disposed in mechanical cooperation with the fixation mechanism, and includes at least one light disposed on the expandable member, and a switch in electrical communication with the at least one light. Distal translation of the collar relative to the elongated portion of the cannula body causes the expandable member to move from a first position defining a first gap between a mid-portion of the expandable member and the elongated portion of the cannula body, to a second position defining a second gap between the mid-portion of the expandable member and the elongated portion of the cannula body. The second gap is greater than the first gap.

In aspects, the at least one light of the illumination mechanism may include at least four lights.

In disclosed aspects, the switch may be disposed on the collar of the fixation mechanism.

Further, in aspects, the at least one light may be disposed distally of the mid-portion of the expandable member.

In aspects, the expandable member may define a plurality of diamond-shaped openings. Also, in aspects, the least one light may include a plurality of lights, and each light of the plurality of lights may be disposed distally of a widest portion of one diamond-shaped opening of the plurality of diamond-shaped openings.

In additional aspects, the expandable member may define four diamond-shaped openings, the at least one light may include four lights, and each light may be disposed distally of a widest portion of one diamond-shaped opening.

In aspects, the cannula body may include a pin extending therefrom, and the collar may include a cam surface configured to slidingly engage the pin of the cannula body.

In disclosed aspects, the fixation mechanism may include a biasing element. At least a portion of the biasing element may be disposed proximally of the collar and may be configured to bias the collar distally.

The present disclosure also relates to a surgical access device including a cannula body, a fixation mechanism, and an illumination mechanism. The cannula body includes a housing and an elongated portion extending distally from the housing. The elongated portion defines a longitudinal axis, and defines a channel extending therethrough. The fixation mechanism is disposed in mechanical cooperation with the elongated portion of the cannula body, and includes an expandable member radially surrounding a portion of the elongated portion of the cannula body. The illumination mechanism is disposed in mechanical cooperation with the fixation mechanism and includes at least one light disposed on the expandable member, and a switch in electrical communication with the at least one light. The at least one light of the illumination mechanism is movable from a first position where the at least one light faces a first direction relative to the cannula body, to a second position where the at least one light faces a second direction relative to the cannula body.

In aspects, when the at least one light is in the first position, the at least one light may face perpendicularly to the longitudinal axis. Further, in aspects, when the at least one light is in the second position, the at least one light may face parallel to the longitudinal axis.

In disclosed aspects, the expandable member may be movable from a first position defining a first gap between a mid-portion of the expandable member and the elongated portion of the cannula body, to a second position defining a second gap between the mid-portion of the expandable member and the elongated portion of the cannula body. The second gap is greater than the first gap. Further, in aspects, movement of the expandable member from the first position to the second position may cause the at least one light to move from the first position to the second position.

Also, in aspects, the fixation mechanism may include a collar at least partially surrounding a portion of the elongated portion of the cannula body. The collar may be longitudinally translatable relative to the elongated portion. Distal translation of the collar relative to the elongated portion may cause the expandable member to move from the first position to the second position. The switch of the illumination mechanism may be disposed on the collar.

In aspects, the at least one light may be disposed distally of a longitudinal mid-point of the expandable member.

In disclosed aspects, when the at least one light is in the second position, the at least one light may face distally.

In further aspects, the expandable member may define a plurality of diamond-shaped openings. Also, in aspects, the least one light may include a plurality of lights, and each light of the plurality of lights may be disposed distally of a widest portion of one diamond-shaped opening of the plurality of diamond-shaped openings.

In aspects, the expandable member may define four diamond-shaped openings.

The at least one light may include four lights, and each light may be disposed distally of a widest portion of one diamond-shaped opening.

DESCRIPTION OF THE DRAWINGS

Various aspects of the present disclosure are illustrated herein with reference to the accompanying drawings, wherein:

FIG. 7 is longitudinal cross-section view of the area of detail indicated in FIG. 6;

FIG. 8 is a side view of a surgical access device illustrating a fixation assembly in an undeployed configuration in accordance with a second aspect of the present disclosure;

DETAILED DESCRIPTION

Figure 1:
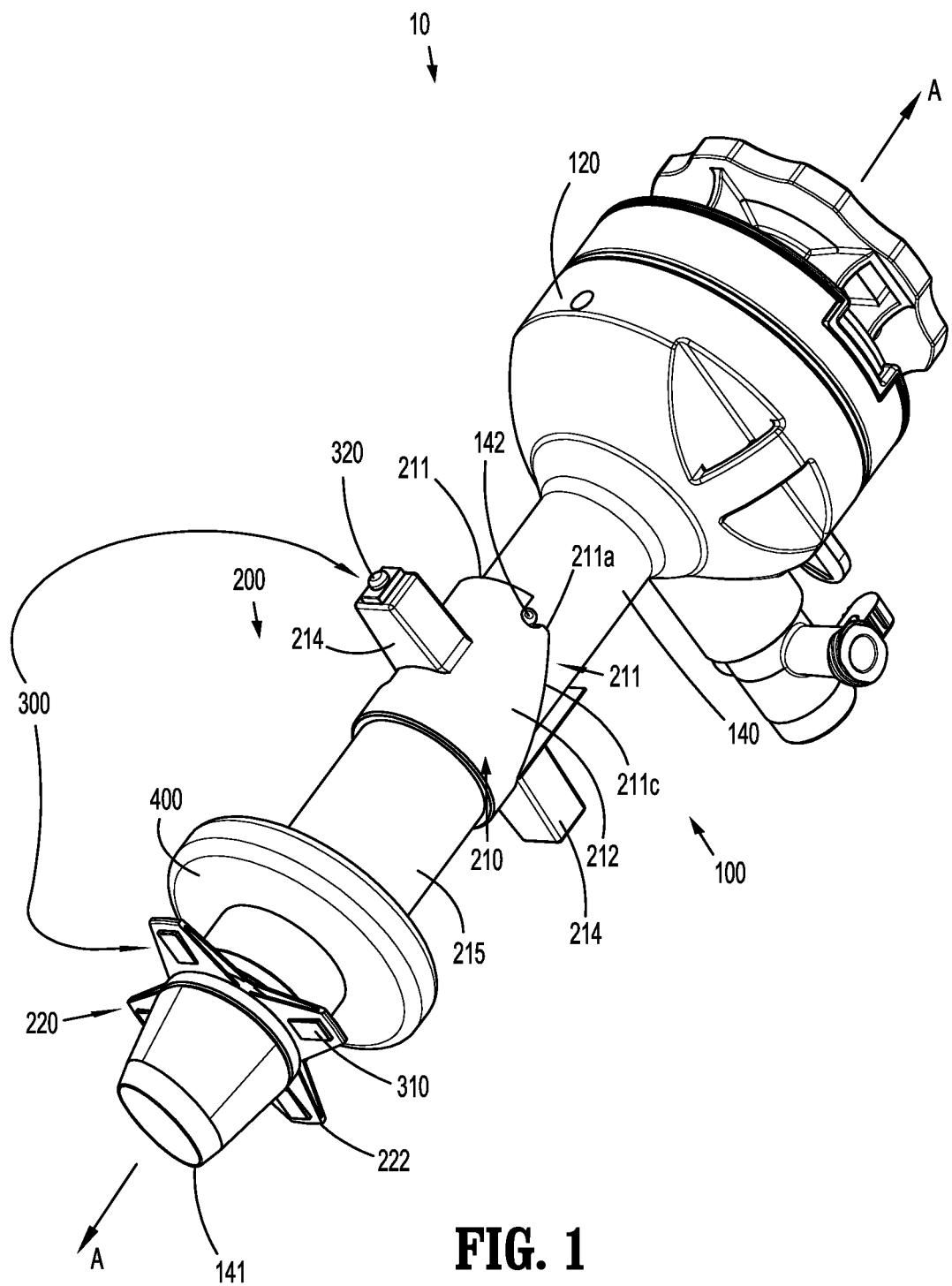
FIG. 1 is a perspective view of a surgical access device illustrating a fixation assembly in a deployed configuration in accordance with a first aspect of the present disclosure.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user. As used herein, the terms "parallel" and "perpendicular" are understood to include relative configurations that are substantially parallel and substantially perpendicular up to about + or −10 degrees from true parallel and true perpendicular, respectively, for example.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial configuration, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

FIGS. 1-7 illustrate a surgical access device according to a first aspect of the present disclosure. With initial reference to FIGS. 1 and 2, the surgical access device 10 includes a cannula body 100, a fixation mechanism 200, and an illumination mechanism 300. The cannula body 100 includes a proximal housing 120 at its proximal end and includes an elongated portion 140 extending distally from the proximal housing 120. The elongated portion 140 defines a channel 150 (FIG. 2) extending therethrough, and defines a longitudinal axis "A-A." An obturator (not shown) is insertable through the channel 150 and is engageable with the proximal housing 120, for instance.

The fixation mechanism 200 is positionable around the elongated portion 140 of the cannula body 100 such that such that the fixation mechanism 200 radially surrounds a portion of the elongated portion 140. More particularly, portions of the fixation mechanism 200 are longitudinally translatable relative to the elongated portion 140 between a first position, where a proximal part 211 of a collar 210 of the fixation mechanism 200 is farther away from a distal tip 141 of the elongated portion 140 and where a mid-portion 222 of an expandable member 220 of the fixation mechanism 200 is closer to the longitudinal axis "A-A" (FIGS. 2-5), and a second position, where the proximal part 211 of the collar 210 is closer to the distal tip 141 of the elongated portion 140 and where the mid-portion 222 of the expandable member 220 is farther away from the longitudinal axis "A-A" (FIGS. 1, 6 and 7).

Figure 2:
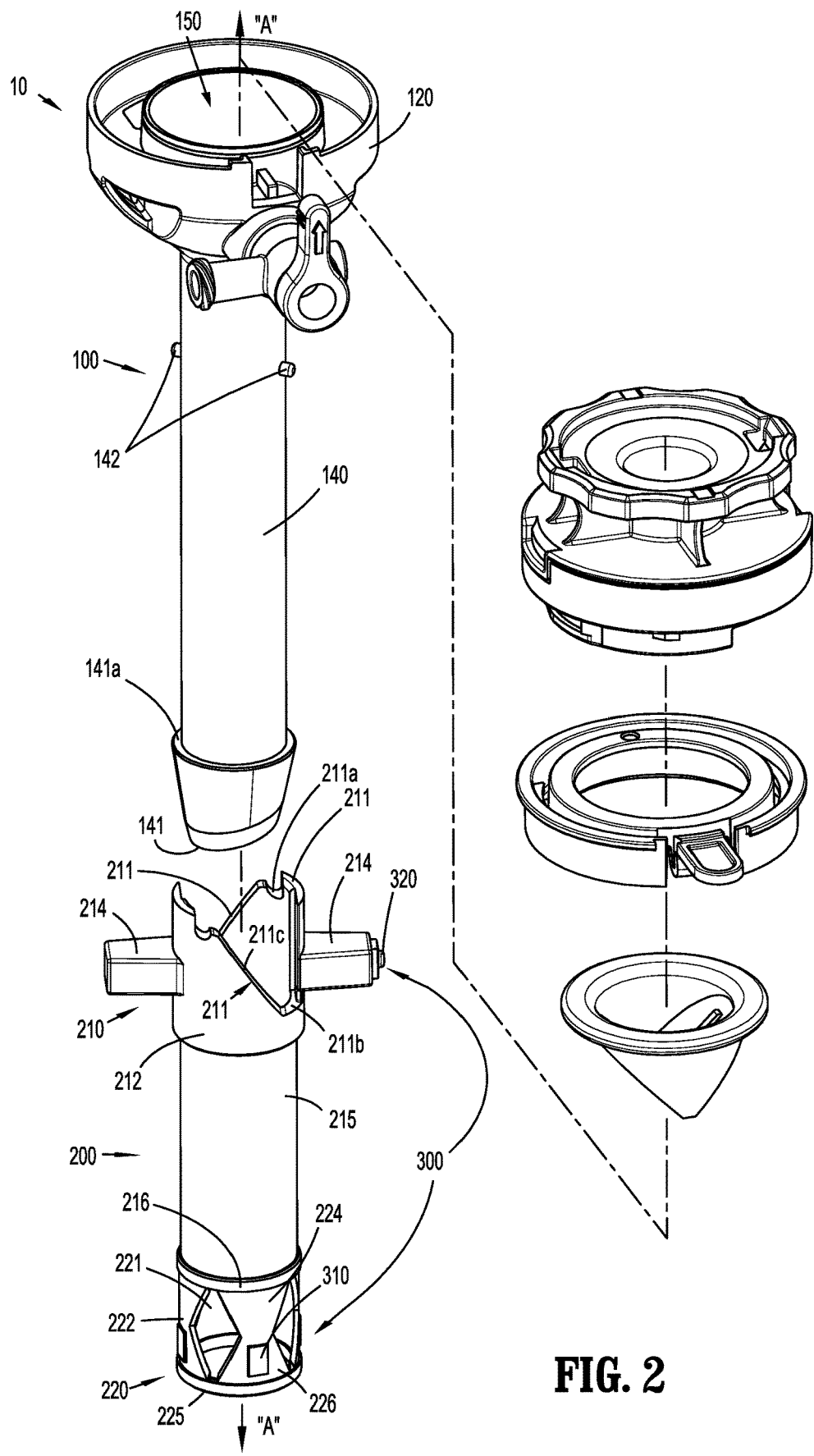
FIG. 2 is an assembly view of the surgical access device of FIG. 1.
Figure 3:
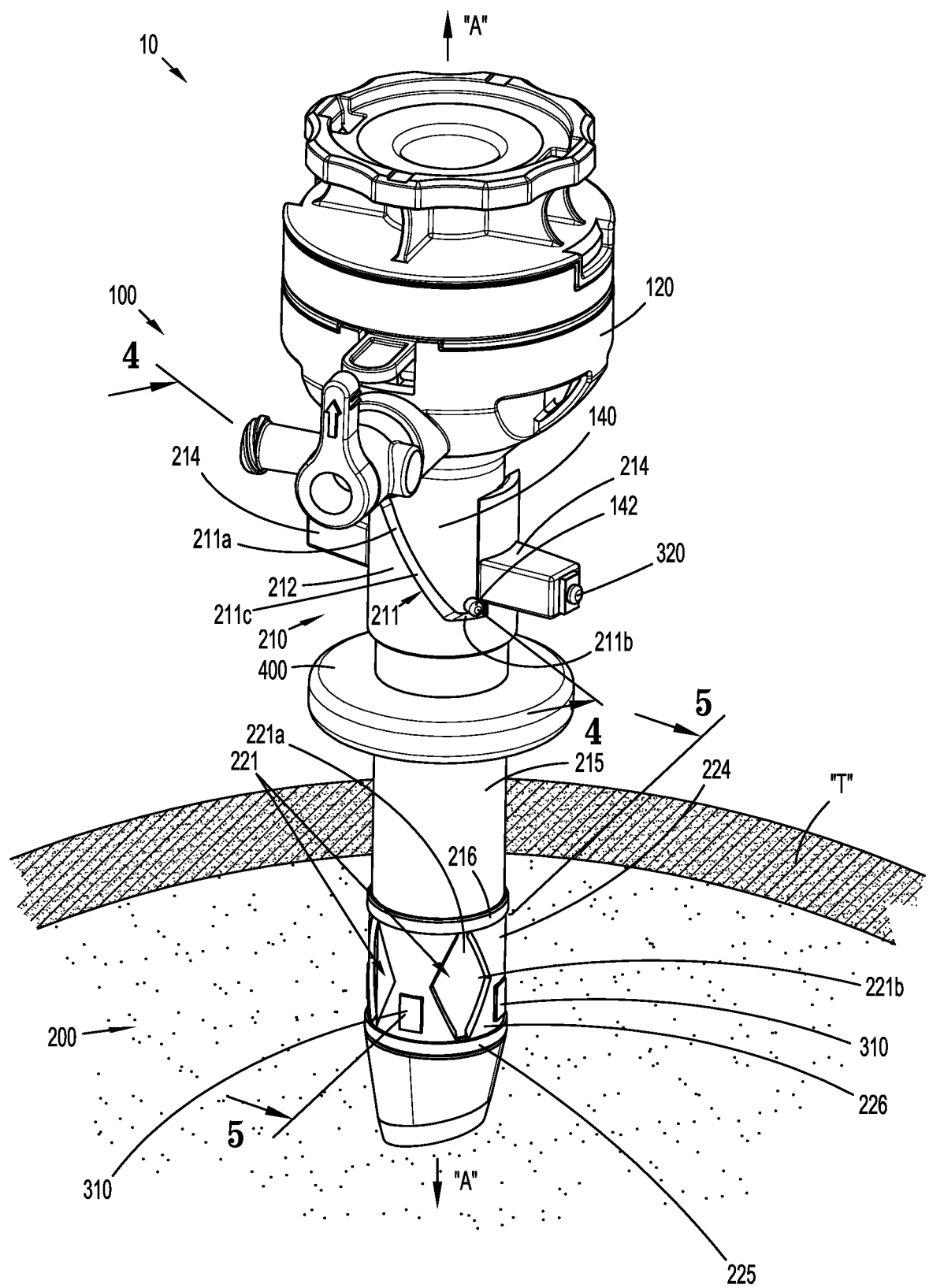
FIG. 3 is a perspective view of the surgical access device of FIG. 1 illustrating the fixation assembly within tissue in an undeployed configuration.

The expandable member 220 defines a plurality of diamond-like openings 221 around its perimeter (FIGS. 2 and 3). The openings 221 are configured such that narrow portions 221a thereof are located at a proximal end 224 and a distal end 226 of the expandable member 220, and a wide portion 221b of each opening 221 is located at or near the mid-portion 222 of the expandable member 220. This configuration allows or facilitates the expandable member 220 to effectively bend or fold (and unfold) at or near its mid-portion 222 as the fixation mechanism 200 transitions between its first position and its second position. In aspects, the expandable member 220 includes a perforation or crease at or near the mid-portion 222 to further facilitate bending and/or folding.

In various aspects, the expandable member 220 is made of rubber or plastic. Such a rubber or plastic expandable member 220 is able to retain its shape (in both the first position and the second position) without the need for the expandable member 220 to be filled with fluid (e.g., liquid or gas), for instance.

Referring to FIGS. 1 and 2, the engagement between the fixation mechanism 200 and the cannula body 100 is shown. The fixation mechanism 200 includes the collar 210, a sleeve 215 extending distally from the collar 210, a proximal ring 216 disposed at a distal end of the sleeve 215, the expandable member 220, and a distal ring 225. The proximal end 224 of the expandable member 220 is engaged with (e.g., affixed to) the proximal ring 216, and the distal end 226 of the expandable member 220 is engaged with (e.g., affixed to) the distal ring 225.

The collar 210, the sleeve 215, and the proximal ring 216 are longitudinally translatable relative to the elongated portion 140 of the cannula body 100 and are rotatable about the longitudinal axis "A-A" relative to the elongated portion 140. The expandable member 220 and the distal ring 225 are also rotatable about the longitudinal axis "A-A" relative to the elongated portion 140. A lip 141a of the distal tip 141 of the elongated portion 140 restricts distal movement of the distal ring 225 relative to the elongated portion 140. As discussed in further detail below, distal movement of the proximal end 224 of the expandable member 220 relative to the elongated portion 140 causes the mid-portion 222 of the expandable member 220 to move away from the longitudinal axis "A-A."

With reference to FIGS. 1-3, further details of the collar 210 of the fixation mechanism 200 are shown. The collar 210 is a ring-like structure that radially surrounds a portion of the elongated portion 140 of the cannula body 100. The collar 210 includes a body 212, a pair of arms 214 extending radially outward from the body 212, and a pair of cam surfaces 211. The arms 214 are configured to be grasped by a user to facilitate rotating the collar 210 about the longitudinal axis "A-A," and to facilitate translating the collar 210 longitudinally in a direction parallel to the longitudinal axis "A-A."

Each cam surface of the pair of cam surfaces 211 of the collar 210 is configured to slidingly engage a respective pin 142 extending radially outward from the elongated portion 140 of the cannula body 100. Each cam surface of the pair of cam surfaces 211 includes a proximal portion 211a, a distal portion 211b, and a connecting portion 211c, which interconnects the proximal portion 211a and the distal portion 211b (FIG. 2). Rotation and distal translation of the collar 210 relative to the elongated portion 140 causes the pair of cam surfaces 211 to move relative to the pins 142 from a first position where each pin 142 is within the distal portion 211b of each cam surface 211 (FIG. 3), which corresponds to the expandable member 220 being in the first, non-expanded position, to a second position (i.e., collapsed position) where each pin 142 is within the proximal portion 211a of each cam surface 211 (FIG. 1), which corresponds to the expandable member 220 being in the second, expanded position.

Further, the collar 210 is biased proximally into the first position (FIG. 3) (e.g., by the material properties of the expandable member 220), such that the distal portion 211b of the cam surface 211 is urged into the pin 142 of the elongated portion 140 of the cannula body 100, thereby restricting proximal movement of the collar 210 relative to the elongated portion 140. When the collar 210 is in the second position (FIG. 1), the proximal portion 211a of the cam surface 211, which includes a valley or detent, is urged into the pin 142 of the elongated portion 140 thereby restricting proximal movement of the collar 210 relative to the elongated portion 140. The connecting portion 211c of the cam surface 211 guides the movement of the collar 210 relative to the pin 142 between the first and second positions of the collar 210.

The collar 210 is fixedly engaged with the sleeve 215, such that rotational and longitudinal movement of the collar 210 relative to the elongated portion 140 translates to a corresponding rotational and longitudinal movement of the sleeve 215. Additionally, the proximal ring 216 is fixedly engaged with the sleeve 215 such that rotational and longitudinal movement of the sleeve 215 translates to a corresponding rotational and longitudinal movement of the proximal ring 216.

Figure 4:
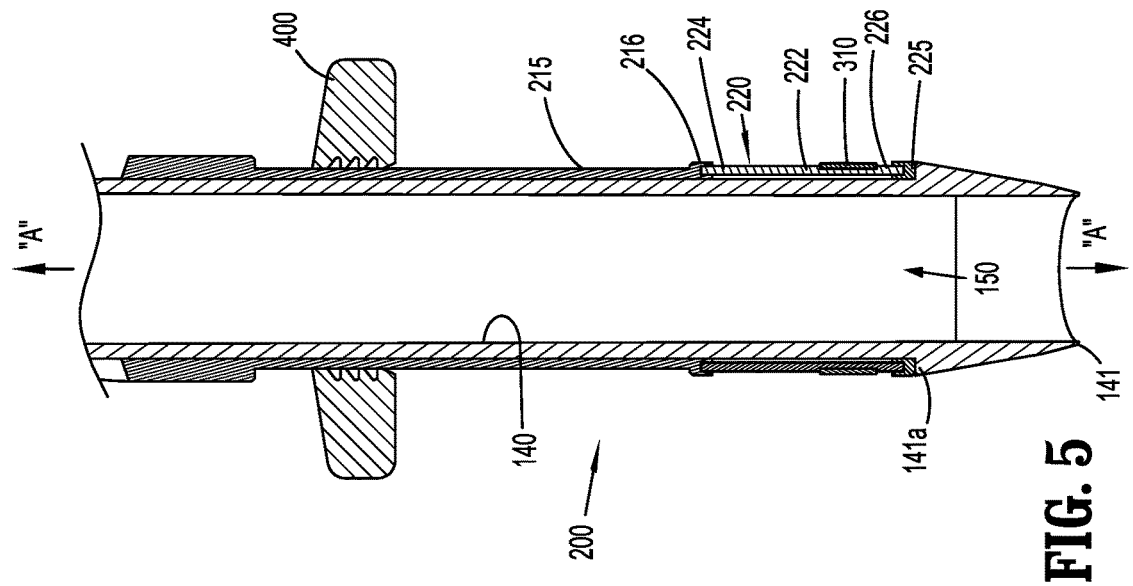
FIG. 4 is a longitudinal cross-sectional view of a portion of the surgical access device taken along section line 4-4 in FIG. 3.
Figure 5:
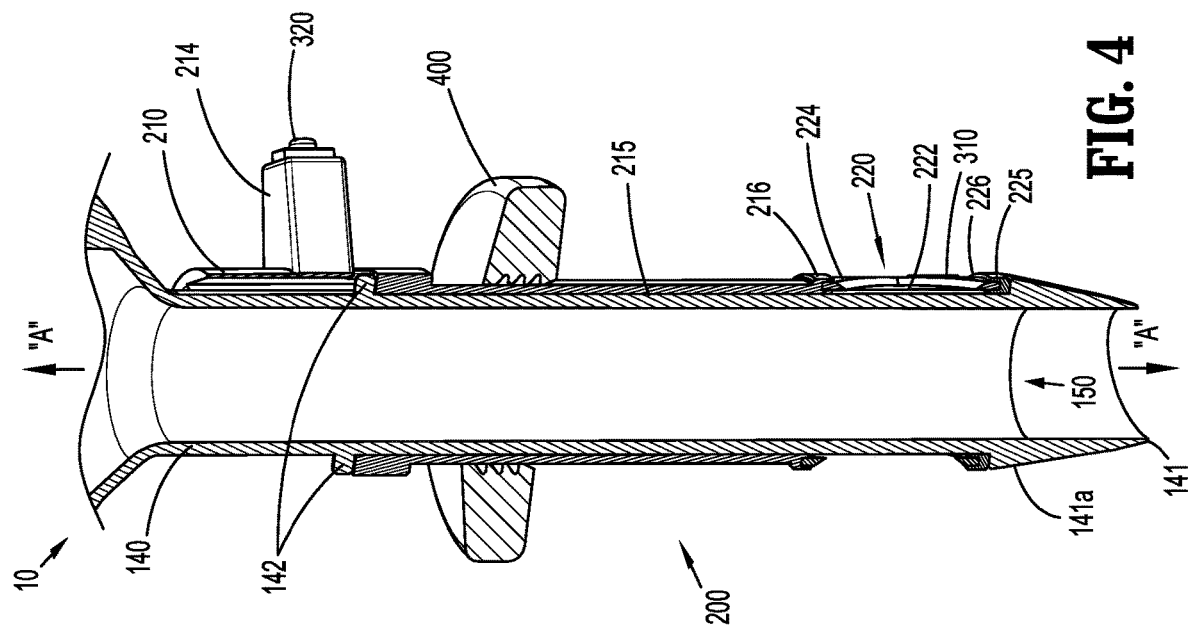
FIG. 5 is a longitudinal cross-sectional view of a portion of the surgical access device taken along section line 5-5 in FIG. 3.
Figure 6:
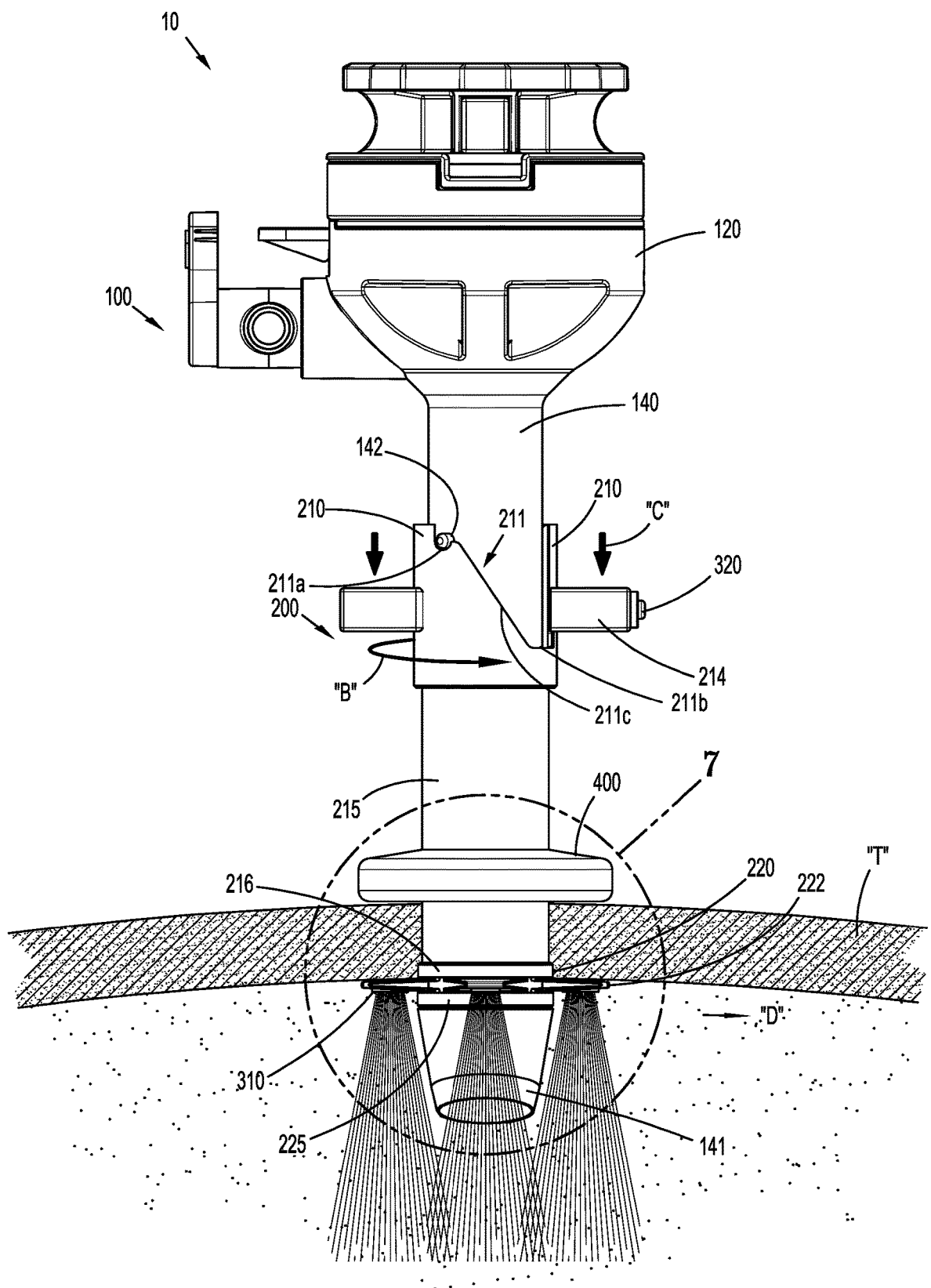
FIG. 6 is a side view of the surgical access device of FIG. 1 illustrating the fixation assembly within tissue in a deployed configuration and with an illumination mechanism providing illumination.

With particular reference to FIGS. 4, 5, and 7, the expandable member 220 is sandwiched between the proximal ring 216 and the distal ring 225. As noted above, the distal ring 225 is fixed from moving distally relative to the elongated portion 140 of the cannula body 100 due to its engagement with the lip 141a of the distal tip 141 of the elongated portion 140. Accordingly, as the proximal ring 216 is moved distally, the expandable member 220 becomes longitudinally compressed such that the expandable member 220 moves from its first position (FIGS. 4 and 5) where the mid-portion 222 of the expandable member 220 is in contact with, close to, or adjacent the elongated portion 140, to its second position (FIG. 7) where the mid-portion 222 of the expandable member 220 is farther away from the elongated portion 140.

Referring to FIGS. 1-3, 6, and 7 various details of the illumination mechanism 300 are shown. Illumination mechanism 300 includes a plurality of lights 310 (e.g., light-emitting diodes (LEDs)) disposed on the expandable member 220, and a switch 320. In the illustrated embodiment, the switch 320 is disposed on one of the arms 214 of the collar 210. In further aspects, the switch 320 may be disposed on a different portion of the surgical access device 10 (e.g., the proximal housing 120). Additionally, a battery (not explicitly shown) may be housed at least partially within one of the arms 214, and/or at least one wire may extend between the switch 320 and the lights 310. For instance, the at least one wire way may extend between the sleeve 215 and the elongated portion 140 of the cannula body (e.g., within a groove of the sleeve 215).

As shown in FIGS. 1-5, for example, the lights 310 are disposed distally of the mid-portion 222 of the expandable member 220 and are configured to selectively emit light. The switch 320 allows a user to turn on or off the lights 310, as desired. When the expandable member 220 is in its first position (FIGS. 2-5), the lights 310 face sideways, generally perpendicularly to the longitudinal axis "A-A."

With particular reference to FIGS. 1, 6 and 7, when the expandable member 220 is in its second position, the lights 310 face distally. Thus, as the expandable member 220 moves between its first position and its second position, the lights 310 correspondingly move between a first position where the lights 310 face sideways, and a second position where the lights 310 face distally. Additionally, when the lights 310 are in the first position, the lights 310 are spaced a first distance from the longitudinal axis "A-A," and when the lights 310 are in the second position, the lights 310 are spaced a second distance from the longitudinal axis "A-A"; the second distance is greater than the first distance.

Referring now to FIGS. 1 and 3-7, an anchor 400 is shown. The anchor 400 is positionable around the elongated portion 140 of the cannula body 100 such that the anchor 400 radially surrounds a portion of the elongated portion 140. The anchor 400 can either have a frictional engagement with the elongated portion 140 such that the anchor 400 can be pushed/pulled to move between longitudinal positions, or the anchor 400 can be rotationally engaged with the elongated portion 140 (e.g., a threaded connection) such that the anchor 400 can be rotated about the longitudinal axis "A-A" relative to the elongated portion 140 to move between longitudinal positions. The anchor 400 may also be fixed from longitudinal and/or rotational movement relative to the elongated portion 140.

In use, when the fixation mechanism 200 is in its first position (FIGS. 2-5), corresponding to the collar 210, the expandable member 220, and the lights 310 being in their first positions, the distal tip 141 of the elongated portion 140 of the cannula body 100 is inserted through an incision in tissue. Engagement between the anchor 400 and a proximal wall of the tissue "T" prevents additional insertion of the cannula body 100.

To transition the fixation mechanism 200 and the lights 310 to their second position (FIGS. 1, 6 and 7), a user rotates the collar 210 in the general direction of arrow "B" (FIG. 6) relative to the elongated portion 140 of the cannula body 100, and (e.g., simultaneously) pushes the collar 210 distally in the general direction of arrow "C" (FIGS. 6 and 7). This movement of the collar 210 relative to the elongated portion 140 causes the pins 142 of the elongated portion 140 to move along the respective cam surfaces 211 of the collar 210, from the distal portion 211b, along the connecting portion 211c, and into the proximal portion 211a of the cam surfaces 211 such that the pins 142 are nestled in the detents. The distal movement of the collar 210 also causes the sleeve 215 and proximal ring 216 to move distally relative to the elongated portion 140 and relative to the distal ring 225. Further, as discussed above, this distal movement causes the mid-portion 222 of the expandable member 220 to move in the general direction of arrow "D" (FIG. 6), away from the elongated portion 140. In this position, the surgical access device 10 can be moved proximally relatively to the tissue such that the expandable member 220 engages a distal portion of the tissue wall "T."

The lights 310 may be switched on or off by a user via the switch 320 at any stage during use. It may be helpful to have the lights 310 in the on position when the expandable member 220 is in its second, expanded position (FIGS. 1, 6 and 7) and after the distal tip 141 of the elongated portion 140 of the cannula body 100 is with tissue, for instance, to help a user more clearly view the target tissue, as shown in FIGS. 6 and 7.

Next, in aspects where the anchor 400 is longitudinally movable relative the elongated portion 140 of the cannula body 100, the anchor 400 is moved distally such that the anchor 400 contacts a proximal portion of the tissue wall, thereby sandwiching the tissue wall between the anchor 400 and the expandable member 220, and fixing the longitudinal position of the cannula body 100 relative to the tissue wall.

Figure 9:
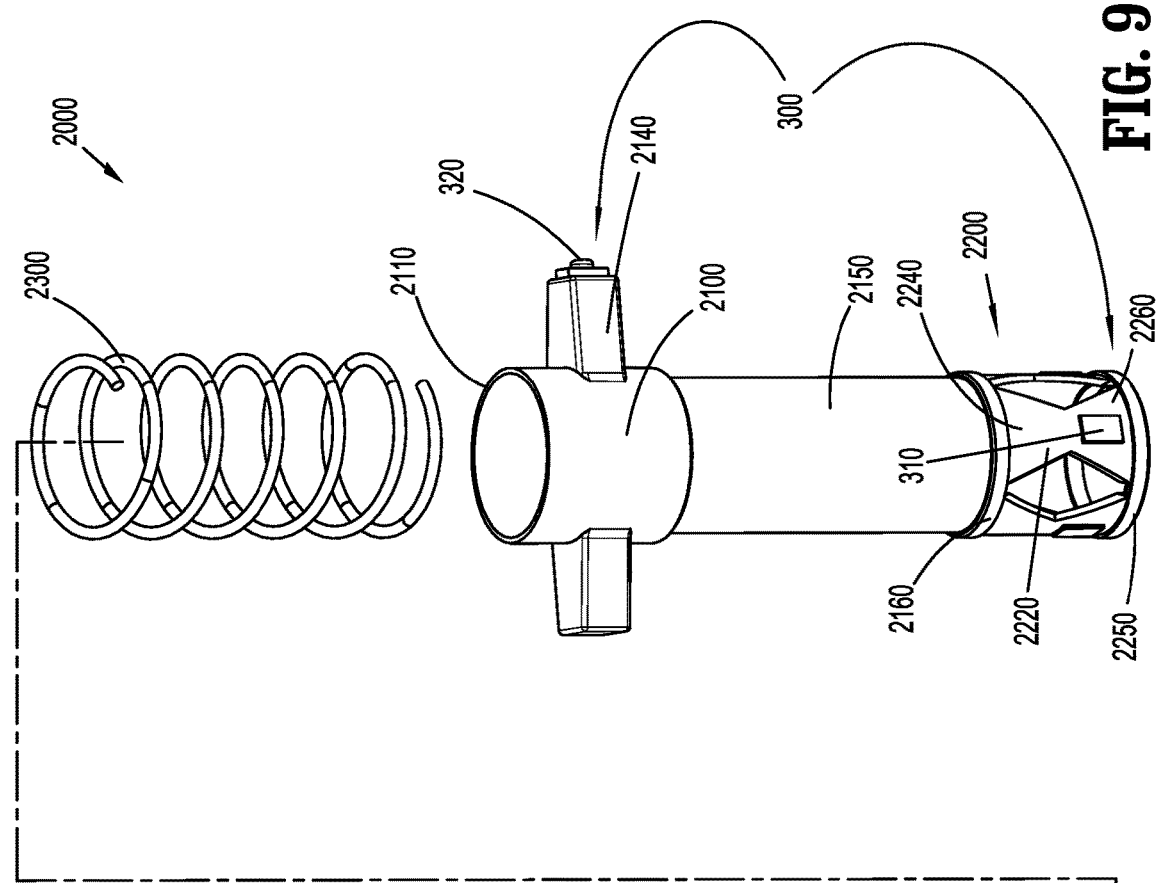
FIG. 9 is an assembly view of the surgical access device of FIG. 8.
Figure 9:
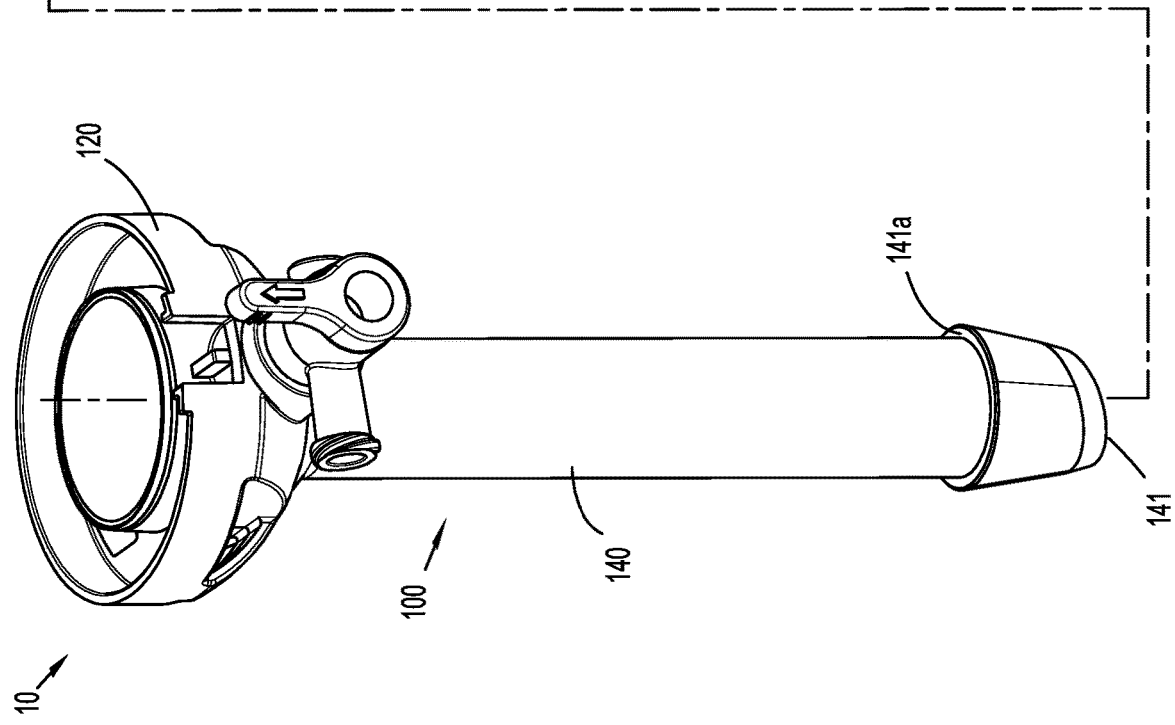
Figure 10:
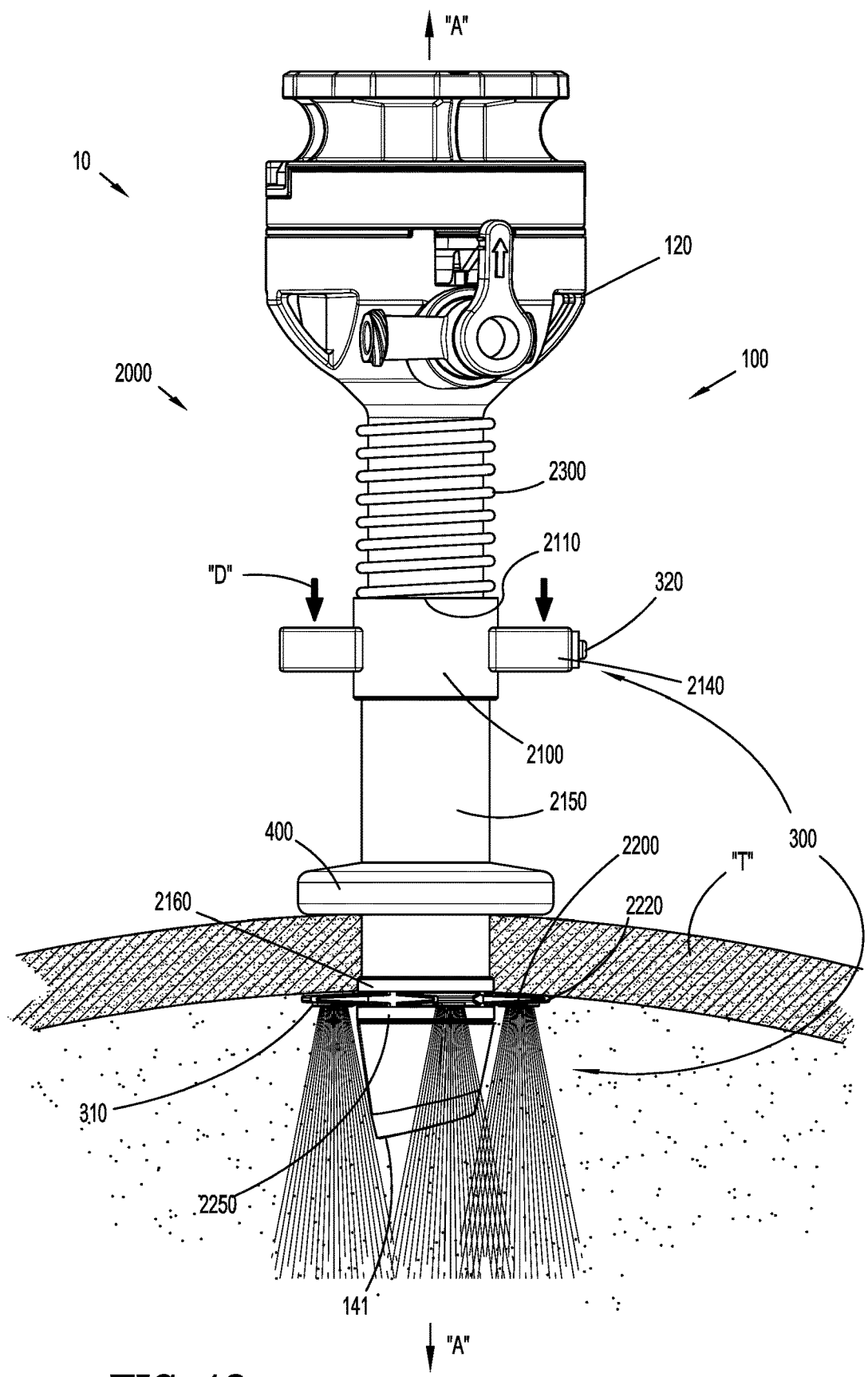
FIG. 10 is a side view of the surgical access device of FIG. 8 illustrating the fixation assembly within tissue in a deployed configuration and with an illumination mechanism providing illumination.

FIGS. 8-10 illustrate a second aspect of a fixation mechanism 2000 for use with the surgical access device 10 according to the present disclosure. The fixation mechanism 2000 is positionable around the elongated portion 140 of the cannula body 100 such that such that the fixation mechanism 2000 radially surrounds a portion of the elongated portion 140. More particularly, portions of the fixation mechanism 2000 are longitudinally translatable along the elongated portion 140 between a first position where a proximal part 2110 of a collar 2100 of the fixation mechanism 2000 is farther away from the distal tip 141 of the elongated portion 140 and where a mid-portion 2220 of an expandable member 2200 of the fixation mechanism 2000 is closer to the longitudinal axis "A-A" (FIG. 8), and a second position, where the proximal part 2110 of the collar 2100 is closer to the distal tip 141 of the elongated portion 140 and where the mid-portion 2220 of the expandable member 2200 is farther away from the longitudinal axis "A-A" (FIG. 10). Additionally, the illumination mechanism 300 (including the plurality of lights 310 and the switch 320) and the anchor 400 are usable with the fixation mechanism 2000 in the same or similar manner the illumination mechanism 300 are the anchor 400 are usable with the fixation mechanism 2000, as discussed above with regard to the fixation mechanism 200.

Various aspects of the fixation mechanism 2000 are the same or similar to those of the fixation mechanism 200, discussed above. Accordingly, only the main differences will be discussed in detail herein.

With continued reference to FIGS. 8-10, the fixation mechanism 2000 includes the collar 2100, a sleeve 2150 extending distally from the collar 2100, a proximal ring 2160 disposed at a distal end of the sleeve 2150, the expandable member 2200, a distal ring 2250, and a biasing element 2300. A proximal end 2240 of the expandable member 2200 is engaged with (e.g., affixed to) the proximal ring 2160, and a distal end 2260 of the expandable member 2200 is engaged with (e.g., affixed to) the distal ring 2250.

The collar 2100, the sleeve 2105, and the proximal ring 2160 are longitudinally translatable relative to the elongated portion 140 of the cannula body 100. The lip 141a (FIG. 9) of the distal tip 141 of the elongated portion 140 restricts distal movement of the distal ring 2250 relative to the elongated portion 140. Similar to the fixation mechanism 200 discussed above, distal movement of the proximal end 2240 of the expandable member 2200 relative to the elongated portion 140 causes the mid-portion 2220 of the expandable member 2200 to move away from the longitudinal axis "A-A."

The biasing element 2300 (e.g., a compression spring) radially surrounds the elongated portion 140 of the cannula body 100, and is positioned between a distal portion of the proximal housing 120 and a proximal portion of the collar 2100 of the fixation mechanism 2000. The biasing element 2300 biases the collar 2100 distally relative to the elongated portion 140, in the general direction of arrow "D" in FIG. 10, such that the expandable member 2200 is biased towards its second position (FIG. 10). To overcome the bias of the biasing element 2300, a user pulls arms 2140 of the collar 2100 proximally relative to the elongated portion 140, in the general direction of arrow "E" in FIG. 8, such that the expandable member 2200 moves towards its first position (FIG. 8).

In use, when the fixation mechanism 2000 is in its first position (FIG. 8), corresponding to the expandable member 2200, and the lights 310 being in their first positions, and the biasing element 2300 being in the compressed orientation (e.g., a user is pulling the arms 2140 of the collar 2100 proximally), the distal tip 141 of the elongated portion 140 of the cannula body 100 is inserted through an incision in tissue. Engagement between the anchor 400 and a proximal wall of the tissue prevents additional insertion of the cannula body 100.

To transition the fixation mechanism 2000 and the lights 310 to their second position (FIG. 10), the user releases the proximal force exerted on the arms 2140, thereby allowing the biasing element 2300 to expand distally into its second orientation, which moves the collar 2100 distally. This distal movement of the collar 2100 relative to the elongated portion 140 causes the sleeve 2150 and proximal ring 2160 to move distally relative to the elongated portion 1400 and relative to the distal ring 2250. Further, as discussed above, this distal movement causes the mid-portion 2220 of the expandable member 2200 to move away from the elongated portion 140. In this position, the surgical access device 10 can be moved proximally relatively to the tissue "T" such that the expandable member 2200 engages a distal portion of the tissue wall (FIG. 10).

The lights 310 may be switched on or off by a user via the switch 320 at any stage during use. It may be helpful to have the lights 310 in the on position when the expandable member 2200 is in its second, expanded position and after the distal tip 141 of the elongated portion 140 of the cannula body 100 is with tissue, for instance, to help a user more clearly view the target tissue, as shown in FIG. 10.

Next, in aspects where the anchor 400 is longitudinally movable relative the elongated portion 140 of the cannula body 100, the anchor 400 is moved distally such that the anchor 400 contacts a proximal portion of the tissue wall "T," thereby sandwiching the tissue wall "T" between the anchor 400 and the expandable member 2200, and fixing the longitudinal position of the cannula body 100 relative to the tissue wall "T."

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A surgical access device, comprising:
   a cannula body including a housing and an elongated portion extending distally from the housing, the elongated portion defining a longitudinal axis, and defining a channel extending therethrough;
   a fixation mechanism disposed in mechanical cooperation with the elongated portion of the cannula body, the fixation mechanism including:
      a collar at least partially surrounding a portion of the elongated portion of the cannula body, and being longitudinally translatable relative to the elongated portion of the cannula body;
      a sleeve extending distally from the collar;
      an expandable member extending distally from the sleeve and radially surrounding a portion of the elongated portion of the cannula body; and
      a distal ring engaged with a distal portion of the expandable member and longitudinally fixed relative to the elongated portion of the cannula body; and
   an illumination mechanism disposed in mechanical cooperation with the fixation mechanism, the illumination mechanism including:
      at least one light disposed on the expandable member and distally of a mid-portion of the expandable member; and
      a switch in electrical communication with the at least one light;
   wherein distal translation of the collar relative to the elongated portion of the cannula body causes the expandable member to move from a first position defining a first gap between the mid-portion of the expandable member and the elongated portion of the cannula body, to a second position defining a second gap between the mid-portion of the expandable member and the elongated portion of the cannula body, the second gap being greater than the first gap.

2. The surgical access device according to claim 1, wherein the at least one light of the illumination mechanism includes at least four lights.

3. The surgical access device according to claim 1, wherein the switch is disposed on the collar of the fixation mechanism.

4. The surgical access device according to claim 1, wherein the expandable member defines a plurality of diamond-shaped openings.

5. The surgical access device according to claim 4, wherein the least one light includes a plurality of lights, and wherein each light of the plurality of lights is disposed distally of a widest portion of one diamond-shaped opening of the plurality of diamond-shaped openings.

6. The surgical access device according to claim 1, wherein the expandable member defines four diamond-shaped openings, wherein the at least one light includes four lights, and wherein each light is disposed distally of a widest portion of one diamond-shaped opening.

7. The surgical access device according to claim 1, wherein the cannula body includes a pin extending therefrom, and wherein the collar includes a cam surface configured to slidingly engage the pin of the cannula body.

8. The surgical access device according to claim 1, wherein the fixation mechanism includes a biasing element, at least a portion of the biasing element is disposed proximally of the collar and is configured to bias the collar distally.

9. A surgical access device, comprising:
   a cannula body including a housing and an elongated portion extending distally from the housing, the elongated portion defining a longitudinal axis, and defining a channel extending therethrough;
   a fixation mechanism disposed in mechanical cooperation with the elongated portion of the cannula body, the fixation mechanism including an expandable member radially surrounding a portion of the elongated portion of the cannula body, and including a collar at least partially surrounding a portion of the elongated portion of the cannula body and being longitudinally translatable relative to the elongated portion, the expandable member being movable from a first position defining a first gap between a mid-portion of the expandable member and the elongated portion of the cannula body, to a second position defining a second gap between the mid-portion of the expandable member and the elongated portion of the cannula body, wherein the second gap is greater than the first gap; and an illumination mechanism disposed in mechanical cooperation with the fixation mechanism, the illumination mechanism including at least one light disposed on the expandable member, and a switch disposed on the collar and in electrical communication with the at least one light;

wherein the at least one light of the illumination mechanism is movable from a first position where the at least one light faces a first direction relative to the cannula body, to a second position where the at least one light faces a second direction relative to the cannula body, movement of the expandable member from the first position to the second position causes the at least one light to move from the first position to the second position, and distal translation of the collar relative to the elongated portion causes the expandable member to move from the first position to the second position.

10. The surgical access device according to claim 9, wherein when the at least one light is in the first position, the at least one light faces perpendicularly to the longitudinal axis.

11. The surgical access device according to claim 10, wherein when the at least one light is in the second position, the at least one light faces parallel to the longitudinal axis.

12. The surgical access device according to claim 9, wherein the at least one light is disposed distally of a longitudinal mid-point of the expandable member.

13. The surgical access device according to claim 9, wherein when the at least one light is in the second position, the at least one light faces distally.

14. The surgical access device according to claim 9, wherein the expandable member defines a plurality of diamond-shaped openings.

15. The surgical access device according to claim 14, wherein the least one light includes a plurality of lights, and wherein each light of the plurality of lights is disposed distally of a widest portion of one diamond-shaped opening of the plurality of diamond-shaped openings.

16. The surgical access device according to claim 9, wherein the expandable member defines four diamond-shaped openings, wherein the at least one light includes four lights, and wherein each light is disposed distally of a widest portion of one diamond-shaped opening.

17. A surgical access device, comprising:

a cannula body including a housing and an elongated portion extending distally from the housing, the elongated portion defining a longitudinal axis, and defining a channel extending through the elongated portion;

a fixation mechanism disposed in mechanical cooperation with the elongated portion of the cannula body, the fixation mechanism including:
 a collar at least partially surrounding a portion of the elongated portion of the cannula body, and being longitudinally translatable relative to the elongated portion of the cannula body;
 a sleeve extending distally from the collar;
 an expandable member extending distally from the sleeve and radially surrounding a portion of the elongated portion of the cannula body; and
 a distal ring engaged with a distal portion of the expandable member and longitudinally fixed relative to the elongated portion of the cannula body; and an illumination mechanism disposed in mechanical cooperation with the fixation mechanism, the illumination mechanism including:
 at least one light disposed on the expandable member; and
 a switch disposed on the collar of the fixation mechanism and in electrical communication with the at least one light;

wherein distal translation of the collar relative to the elongated portion of the cannula body causes the expandable member to move from a first position defining a first gap between a mid-portion of the expandable member and the elongated portion of the cannula body, to a second position defining a second gap between the mid-portion of the expandable member and the elongated portion of the cannula body, the second gap being greater than the first gap.

* * * * *